US006288065B1

(12) United States Patent
Huth et al.

(10) Patent No.: US 6,288,065 B1
(45) Date of Patent: *Sep. 11, 2001

(54) QUINOXALINE-CARBOXYLIC ACID DERIVATIVES

(75) Inventors: Andreas Huth; Ralph Schmiechen; Ilse Beetz; Ingrid Schumann; Lechoslaw Turski; Peter Andreas Loschmann; David Norman Stephens; Dieter Seidelmann; Martin Kruger; Dieter Rahtz; Peter Holscher, all of Berlin (DE)

(73) Assignee: Schering Aktiengeseellschaft, Berling (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/102,649

(22) Filed: Jun. 23, 1998

Related U.S. Application Data

(63) Continuation of application No. 08/462,763, filed on Jun. 5, 1995, now Pat. No. 6,057,304, which is a continuation of application No. 08/208,058, filed on Mar. 9, 1994, now abandoned, which is a continuation of application No. 07/966,470, filed on Oct. 26, 1992, now abandoned.

(30) Foreign Application Priority Data

Oct. 26, 1991 (DE) .................................. 41 35 871
Jul. 17, 1992 (DE) .................................. 42 24 200

(51) Int. Cl.$^7$ ........................ C07D 241/44; A61K 31/498
(52) U.S. Cl. .................. 514/249; 514/228.2; 514/234.8; 514/241; 514/242; 544/182; 544/215; 544/62; 544/116; 544/119; 544/238; 544/295; 544/354
(58) Field of Search ........................ 544/344, 354, 544/62, 116, 238, 119, 295, 182, 215; 514/249, 250, 228.2, 234.8, 241, 242

(56) References Cited

U.S. PATENT DOCUMENTS

| 5,026,704 | 6/1991 | Honore et al. ............. 544/354 |
| 5,166,155 | 11/1992 | Jorgensen et al. ............ 544/354 |
| 5,283,244 | 2/1994 | Sakamoto et al. ............ 544/354 |
| 5,710,138 | * 1/1998 | Holscher et al. ............ 514/80 |
| 5,955,461 | * 9/1999 | Huth et al. ............ 514/249 |
| 6,057,304 | * 5/2000 | Huth et al. ............ 514/80 |
| 6,096,743 | * 8/2000 | Shishikura et al. ............ 514/249 |
| 6,136,805 | * 10/2000 | Huth et al. ............ 514/249 |
| 6,143,733 | * 11/2000 | Huth et al. ............ 514/85 |

FOREIGN PATENT DOCUMENTS

| 315959 | 11/1988 | (EP) . |
| WO 91/13878 | 9/1991 | (WO) . |
| 92/07847 | 5/1992 | (WO) . |

OTHER PUBLICATIONS

Lees, *Pharmacology and Pathophysiology*, pp. 51–74 (1996).*
Epperson et al, Bioorganic & Medicinal Chemistry Letters, vol. 3, pp. 2801–2804, 1993.*
Acheson et al., J. Chem. Soc. (C), p. 2218 (1996).
Meldrum, Brian S., Current Science Ltd., Current Opinion in Neurology and Neurosurgery, vol. 5, 1992, pp. 508–513.
Akhlag et al., Brain Research Reviews, 16 (1991) pp. 171–191.
Kessler et al., Brain Research 489, pp. 377–382.
Ishida et al., Brain Research, 266 (1983) pp. 174–177.
Kudo and Shibata, Br. J. Pharmac. 1984, 83, pp. 813–820.

\* cited by examiner

*Primary Examiner*—Emily Bernhardt
(74) *Attorney, Agent, or Firm*—Millen, White, Zelano & Branigan, P.C.

(57) ABSTRACT

The disclosure relates to quinoxaline derivates of Formula I (I)

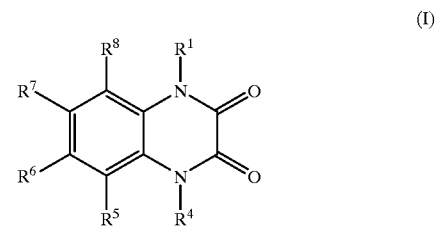

wherein
$R^1, R^4, R^5, R^6, R^7$ and $R^8$ are defined in the disclosure, as well as their production and use in medicinal agents.

9 Claims, No Drawings

QUINOXALINE-CARBOXYLIC ACID DERIVATIVES

CROSS-REFERENCE TO RELATED APPLICATIONS

This application is a continuation of U.S. application Ser. No. 08/462,763, filed Jun. 5, 1995, now U.S. Pat. No. 6,057,304 which is a continuation of U.S. application Ser. No. 08/208,058, filed Mar. 9, 1994, now abandoned, which is a continuation of U.S. application Ser. No. 07/966,470, filed Oct. 26, 1992, now abandoned.

SUMMARY OF THE INVENTION

The invention relates to quinoxalinedione-carboxylic and -phosphonic acid derivatives, their production and use in medicinal agents.

It is known that quinoxaline derivatives exhibit affinity to the quisqualate receptors and are suitable, based on the affinity, as medicinal agents for the treatment of diseases of the central nervous system.

It has now been found that the compounds of this invention, as compared with the quinoxalines known from EP-A-315,959 and WO 91/138 78, are distinguished by their good binding capacity to the quisqualate receptors.

The compounds according to this invention have the Formula I

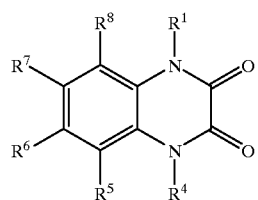

(I)

wherein
- $R^1$ means $R^2$-substituted $C_{1-12}$ alkyl, $R^2$-substituted $C_{2-12}$ alkenyl, $R^2$-substituted $C_{2-12}$ alkynyl, $R^2$-substituted $C_{3-7}$ cycloalkyl, $-(CH_2)_n$-$C_{6-12}$ aryl substituted by $R^2$ in the aryl or in the alkyl residue, or $-(CH_2)_n$ hetaryl substituted by $R^2$ in the hetaryl or alkyl residue,
- $R^4$ means hydrogen, $R^2$-substituted $C_{1-12}$ alkyl, $R^2$-substituted $C_{2-12}$ alkenyl, $R^2$-substituted $C_{2-12}$ alkynyl, $(CH_2)_n$-$C_{6-12}$aryl $R^2$-substituted in the aryl or alkyl residue, or $-(CH_2)_n$ hetaryl $R^2$-substitute in the hetaryl or alkyl residue,
- $R^5$, $R^6$, $R^7$ and $R^8$, being identical or different, mean hydrogen, halogen, nitro, $NR^9R^{10}$, $NHCOR^{11}$, $SO_2R^{12}$, $C_{3-7}$ cycloalkyloxy, $COR^{13}$, cyano, $CF_3$, $C_{1-6}$ alkyl, $C_{1-4}$ alkoxy, or imidazole optionally substituted by cyano, $C_{1-4}$ alkyl or $-COO$-$C_{1-6}$ alkyl, or
- $R^5$ and $R^6$ or $R^7$ and $R^8$ represent a fused benzene ring, wherein
- $R^2$ is $-CO$-$R^3$ or $-PO$-$XY$, $R^2$ being present once to twice in identical or different form, and
- n is 0, 1, 2, 3, 4 or 5, and
- $R^3$ is hydroxy, $C_{1-6}$ alkoxy or $NR^9R^{10}$,
- X and Y, being identical or different, mean hydroxy, $C_{1-6}$ alkoxy, $C_{1-4}$ alkyl or $NR^9R^{10}$, and
- $R^9$ and $R^{10}$, being identical or different, mean hydrogen, $C_{1-4}$ alkyl or jointly with the nitrogen atom form a saturated 5- or 6-membered heterocycle which can contain an additional oxygen, sulfur or nitrogen atom,
- $R^{11}$ means $C_{1-6}$ alkyl or phenyl,
- $R^{12}$ means hydrogen, $C_{1-4}$ alkyl, $NH_2$, $N(C_{1-4}$ alkyl$)_2$ and
- $R^{13}$ means hydroxy, $C_{1-6}$ alkoxy, $C_{1-6}$alkyl or $NR^9R^{10}$, as well as their isomers or salts,
wherein,
- if $R^4$, $R^5$, $R^6$, $R^7$ and $R^8$ mean hydrogen, $R^1$ cannot be carbamoylmethyl, 1-carboxy-1-phenylmethyl, or straight-chain $C_{1-6}$ alkyl substituted in the 1-position by $-COOH$ or $-COO$-$C_{1-6}$ alkyl, and
- if $R^1$ means straight-chain $C_{1-6}$ alkyl substituted in the 1-position by $-COOH$ or $-COO$-$C_{1-6}$ alkyl, $R^6$ and/or $R^7$ and, respectively, $R^6$ and $R^8$ cannot be fluorine, chlorine or bromine, and $R^4$-$R^8$ in each case hydrogen, and
- if $R^1$ is $-CH_2$-$COOH$,
  (a) $R^6$ and $R^7$ cannot be simultaneously methyl or
  (b) $R^6$ or $R^7$ cannot be $NO_2$ and $R^4$-$R^8$ respectively hydrogen.

The compounds of general Formula I also include the possible tautomeric forms and comprise the E or Z isomers or, in case a chiral center is present, the racemates or enantiomers.

The substituents are preferably present in the 6 and/or 7-position.

The $R^2$ substituent is present singly to doubly in identical or different form in any desired position on the alkyl, alkenyl, alkynyl, cycloalkyl, hetaryl or aryl residue.

Alkyl means in each case a straight-chain or branched alkyl residue, such as, for example, methyl, ethyl, propyl, isopropyl, butyl, isobutyl, sec-butyl, tert-butyl, pentyl, isopentyl, hexyl, heptyl, octyl, nonyl, decyl, wherein $C_{1-6}$ alkyl residues are preferred.

Alkenyl includes, in particular, $C_{2-6}$ alkenyl residues which can be straight-chain or branched, such as, for example, 2-propenyl, 2-butenyl, 3-methyl-2-propenyl, 1-propenyl, 1-butenyl, vinyl.

Ethynyl, 1-propynyl, 2-propynyl, 1-butynyl of 2–4 carbon atoms are especially suitable as the alkynyl residues.

$C_{3-7}$ cycloalkyl means in each case cyclo-propyl, cyclobutyl, cyclopentyl, cyclohexyl and cyclo-heptyl, especially $C_{3-5}$ cycloalkyl.

Examples for the aryl residue are phenyl, naphthyl, biphenylyl and indenyl, particularly $(CH_2)_n$-phenyl wherein n=0, 1 or 2.

As the hetaryl residue, suitable are 5- or 6-membered heteroaromatics of 1–3 nitrogen atoms, such as, for example, pyrazole, imidazole, pyrazine, pyridine, pyrimidine, pyridazine, triazine.

Halogen is understood to mean fluorine, chlorine, bromine and iodine.

In case $R^9$ and $R^{10}$ form, jointly with the nitrogen atom, a saturated heterocycle, then this means, for example, piperidine, pyrrolidine, morpholine, thiomorpholine or piperazine.

If $R^1$ means $C_{1-12}$ alkyl and $R^2$ means $COR^3$, then $R^5$–$R^8$ are, in particular, substituents such as $NO_2$, $NR^9R^{10}$, $NHCOR^{11}$, $SO_2R^{12}$, $C_{3-7}$ cycloalkyloxy, $COR^{13}$, cyano, $CF_3$, $C_{1-4}$ alkoxy, optionally substituted imidazole, or a fused benzene ring. The compounds of Formula I wherein $R^2$=$-PO$-$XY$ are distinguished by very good water solubility.

Physiologically compatible salts mean salts of organic and inorganic bases, such as, for example, the well-soluble alkali and alkaline earth salts, as well as N-methylglucamine, dimethylglucamine, ethylglucamine, lysine, 1,6-hexanediamine, ethanolamine, glucosamine, sarcosine, serinol, trishydroxymethylaminomethane, aminopropanediol, Sovak base (2-amino-1, 3, 4-butanetriol), 1-amino-2, 3, 4-butanetriol.

Examples of compounds of formula I include:
3-(6-Nitro-2, 3-dioxo-1,2,3,4-tetrahydroquinoxalin-1-ylmethyl) benzoic acid methyl ester,
1-(3 -ethoxycarbonylpropyl)-6-nitroquinoxaline-2,3-(1H, 4H)-dione,
2-{4-(2-ethoxycarbonylbenzyl)-6-nitro-2,3-dioxo-1,2,3,4-tetrahydroquinoxalin-1-ylmethyl}benzoic acid ethyl ester, and
4-(6-nitro-2,3-dioxo-1,2,3,4-tetrahydroquinoxalin-1-yl) benzoic acid ethyl ester.

High concentrations of excitatory amino acids such as glutamate and aspartate are present in the central nervous system of mammals, including humans, (Fonnum, F., *J. Neurochem,* 42:1–11, 1984). For the excitatory amino acids, various receptors exist which are designated corresponding to their specific agonists as N-methyl-D-aspartate (NMDA), kainate (KA) and quisqualate (QUIS) receptors. The quisqualate receptors are also named AMPA receptors after the specific agonists (RS)α-amino-3-hydroxy -5-methyl-4-isoxazole proportionate. The synaptic function of the excitatory amino acid L-glutamate is also imparted by NMDA receptors.

From clinical and animal-experimental findings, there are indications that in Parkinson's disease (PD), increased glutamatergic neurotransmission occurs in various nuclei of the basal ganglia as a result of the striatal deficiency of dopamine. The neostriatum (NEO) represents the entry structure of the basal ganglia; it obtains from the cortex a massive glutamatergic projection and from the substantia nigra pars compacta (SNC) the dopaminergic nigrostriatal pathway, which degenerates in the case of PD. From the NEO, there are direct pathways to the initial nuclei of the basal ganglia, the internal pallidum link (GPi) and the substantia nigra pars reticulata (SNR), as well as indirect pathways, which run by the external pallidum link (GPe) and nucleus subthalamicus (STH). The STH receives a direct glutamatergic innervation of its own from the cortex; its neurons projecting to the initial nuclei also use L-glutamate as a transmitter.

The synaptic functions of dopamine in NOE are complex. Its effect on the striatal neurons projecting into the GPe is mainly inhibitory, so that as a result of the striatal dopamine deficiency, as it is present in PD, the excitatory glutamatergic influences on these neurons predominate. Since both the striatal pathway to the GPe and the pathway projecting to the STH starting from there are inhibitory, in the case of PD the phenomenon of disinhibition with increase of tonic cellular activity in the STH results. By its glutamatergic projections, the STH finally produces a pathologically increased neuronal activity in the initial nuclei of the basal ganglia. Tests on animal models of PD show that after administration of dopaminergic substances, a normalization of the increased excitatory neurotransmission results, which runs parallel to the "clinical" improvement.

Similar compounds to I are known from WO 91/13878 and EP 315,959.

The compounds of Formula I as well as their physiologically compatible salts are usable as drugs on the basis of their affinity to the quisqualate receptors. By virtue of their activity profile, the compounds of this invention are suitable for the treatment of diseases evoked by hyperactivity of excitatory amino acids, such as glutamate or aspartate. Since the novel compounds act as antagonists of excitatory amino acids and show high specific affinity to the AMPA receptors in that they displace the radiolabeled specific agonist [RS] α-amino-3-hydroxy-5-methyl-4-isoxazole propionate (AMPA) from the AMPA receptors, they are especially suitable for the treatment of diseases that can be affected by way of the receptors of excitatory amino acids, especially the AMPA receptor, such as, for example, Parkinson's disease, Alzheimer's disease, Huntington's disease, epilepsy, hypoglycemia, psychoses, muscular rigidity, emesis, painful conditions, anoxia, and deficits after ischemia.

The affinity of the compounds according to this invention to central AMPA receptors was tested in vitro in classical binding studies. They bind with high affinity to binding sites labeled with $^3$H-AMPA.

In order to test the quality of effectiveness and the efficacy in vivo, the compounds were tested upon intravenous administration to mice. After pre-treatment with the compounds of this invention, the spasms triggered by intracerebroventricular injection of AMPA are antagonized in dependence on the dose.

These findings demonstrate that the compounds constitute potent centrally active AMPA antagonists. They are thus suitable for the treatment of pathological conditions accompanying a disturbance in the glutamate metabolism. In particular, they are suited for the treatment of cerebral ischemia of varying genesis, Parkinson's disease, and also the other diseases recited in the preceding paragraph.

In order to use the compounds of this invention as medicinal agents, they are brought into the form of a pharmaceutical preparation containing, besides the active ingredient, pharmaceutical, organic or inorganic, inert excipients suitable for enteral or parenteral administration, such as, for example, water, gelatin, gum arabic, lactose, amylose, magnesium stearate, talc, vegetable oils, polyalkylene glycols, etc. The pharmaceutical preparations can be present in solid form, e.g. as tablets, dragees, suppositories, capsules, or in the liquid form, e.g. as solutions, suspensions, or emulsions. They moreover contain optionally auxiliary agents, such as preservatives, stabilizers, wetting agents, or emulsifiers, salts for altering osmotic pressure, or buffers.

Suitable for parenteral administration are, in particular, injection solutions or suspensions, particularly aqueous solutions of the active compounds in polyhydroxyethoxylated castor oil.

Also surface-active auxiliary agents can be utilized as the vehicle systems, such as salts of the bile acids, or animal or vegetable phospholipids, but also mixtures thereof, as well as liposomes or their components.

Especially suitable for oral administration are tablets, dragees or capsules with talc and/or a hydrocarbon vehicle or binder, such as, for example, lactose, cornstarch or potato starch. Use in liquid form is likewise possible, e.g. as an elixir to which a sweetener is optionally added.

Especially advantageous is the combination with usual anti-parkinson agents such as L-DOPA, L-DOPA in combination with benserazide and dopaminergic agonists, such as, for example, lisuride, bromocryptine, pergolide, terguride, ropinirol, N-0437 (2[N, n-propyl-N-2-(2-thienyl) ethylamino]-5-hydroxy-tetraline, cabergoline as well as anticholinergic agents.

By combination of the pharmaceutical agents according to the invention with usual anti-parkinson agents, the dose of the usual pharmaceutical agent to be administered is reduced and its effect is increased. The synergistic effect of the combination preparations therefore makes possible an earlier occurrence of the desired effect and a reduction of the side effects. The effect then observed is more pronounced and sustained longer than after single administration of the individual components.

The active compounds can vary in their dosage depending on administration, age and weight of patient, type and severity of the disease to be treated, and similar factors. The daily dose is 0.5–1,000 mg, preferably 50–200 mg; the dosage can be administered as a single dose, given once, or divided into two or more daily doses.

The compounds according to this invention are prepared according to methods known per se. For example, compounds of Formula I are obtained in that (a) a compound of Formula II

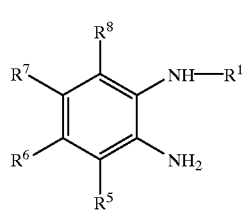

(II)

wherein $R^1$, $R^5$, $R^6$, $R^7$ and $R^8$ have the above-indicated meanings, is cyclized with reactive oxalic acid derivatives and optionally reacted with $R^{4'}$-X wherein X means halogen, tosylate, mesylate or triflate and $R^{4'}$ means $R^4$ with the exception of hydrogen, or (b) a compound of Formula III

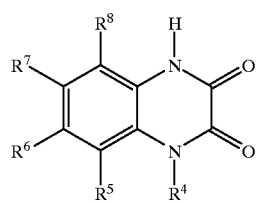

(III)

wherein $R^4$, $R^5$, $R^6$, $R^7$ and $R^8$ have the above-disclosed meanings, is reacted with $R^1$-X to compounds of Formula I and, if desired, the ester group is saponified or the acid group is esterified or amidated or the nitro group is reduced to the amino group or the amino group is alkylated or acylated or the amino group is exchanged for halogen or cyano, or the amino group is reacted with a 2-azabutadiene of Formula IV

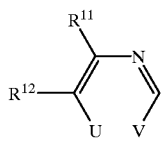

(IV)

wherein U and V represent leaving groups and $R^{11}$ is hydrogen, cyano or $COOC_{1-6}$ alkyl and $R^{12}$ is hydrogen or $C_{1-6}$ alkyl, to obtain an imidazole derivative, or the isomers are separated or the salts are formed.

Cyclization of the compounds of Formula II with a reactive oxalic acid derivative takes place in one stage or also in two stages. The two-stage process is considered to be the preferred one wherein the diamine is reacted with an oxalic acid derivative such as the oxalic ester semichloride in polar solvents, such as dimethylformamide or cyclic or acyclic ethers or halogenated hydrocarbons, e.g. tetrahydrofuran, diethyl ether or methylene chloride in the presence of a base, such as organic amines, e.g. triethylamine, pyridine, ethyldiisopropylamine, or diethylaminopyridine. The subsequent cyclization can be performed in alkaline or also acidic fashion, but preferably in an acidic medium; alcohol can be added to the solvent.

The introduction of the substituents $R^1$ and $R^4$ takes place according to the usual alkylation methods by reacting the quinoxalinedione with $R^1$— or $R^{4'}$—X wherein X means tosylate, mesylate or especially triflate or halogen, in the presence of bases at room temperature or an elevated temperature in aprotic solvents. The anion can also be produced before adding $R^1$— or $R^{4'}$—X. Examples of suitable bases are alkali compounds, such as potassium carbonate, sodium hydroxide, alkali alcoholates and, in particular, metal hydrides, such as sodium hydride. The alkali compounds can also be optionally reacted under phase transfer conditions. In case mixtures of compounds with the substituent $R^1$ and/or $R^4$ are obtained, these are separated in the customary way.

Solvents suitable for the reaction are aprotic polar solvents, such as dimethylformamide, N-methylpyrrolidone, but also cyclic ethers, such as dioxane or tetrahydrofuran.

If, in process version (b), the reaction is carried out with 2 moles of $R^1$—X under otherwise analogous reaction conditions, then the substituents $R^1$ and $R^4$ are introduced simultaneously.

The optionally following saponification of an ester group can take place in alkaline or preferably acidic media by hydrolyzing at an elevated temperature up to the boiling temperature of the reaction mixture in the presence of acids, such as highly concentrated aqueous hydrochloric acid, in solvents such as, for example, trifluoroacetic acid or alcohols. Phosphonic acid esters are hydrolyzed preferably by heating in highly concentrated aqueous acids, e.g. concentrated hydrochloric acid or by treatment with trimethylsilyl bromide and subsequent treatment with water.

Esterification of the carboxylic acid or phosphonic acid is effected conventionally with the corresponding alcohol in an acid or in the presence of an activated acid derivative. Examples of activated acid derivatives are acid chloride, imidazolide or anhydride. In case of the phosphonic acids, reaction with ortho esters of the corresponding alcohol is possible. Also the reaction with the chemical addition product of dicyclohexylcarbodiimide and the corresponding alcohol leads to the ester. Methyl esters can be prepared by reaction with diazomethane.

Amidation is performed on the free acids or on their reactive derivatives, such as, for example, acid chlorides, mixed anhydrides, imidazolides or azides by reaction with the corresponding amines at room temperature.

The reduction of the nitro group to the amino group takes place catalytically in polar solvents at room temperature or elevated temperature under hydrogen pressure. Suitable catalysts are metals, such as Raney nickel or noble metal catalysts, such as palladium or platinum, optionally on supports. In place of hydrogen, it is also possible to utilize ammonium formate in a manner known per se. Reducing agents, such as tin(II) chloride or titanium(III) chloride can be used just as well as complex metal hydrides, optionally in the presence of heavy metal salts. It may be advantageous to introduce the ester group prior to the reduction.

If alkylation of the amino group is desired, then an alkylation can be performed in accordance with customary methods, for example with alkyl halogenides. Also reductive amination with an aldehyde and reducing agents such as sodium cyanoborohydride is possible. Acylation likewise takes place according to the conventional methods. For example, the reaction is performed in an aqueous medium in the presence of a base with the corresponding acid anhydrides or acid halogenides.

The cyano group can be introduced with the aid of the Sandmeyer reaction: for example, the diazonium salts formed intermediarily from the amino compounds with nitrites can be reacted with cyanides in the presence of Cu(I) cyanide or with $K_2Ni(CN)_4$.

Introduction of the halogens chlorine, bromine or iodine by way of the amino group can take place in nonaqueous or aqueous fashion: for example, in aqueous fashion according to Sandmeyer by reacting the diazonium salts, formed intermediarily with nitrites, with Cu(I) chloride or Cu(I) bromide in the presence of the corresponding acid, hydrochloric acid or hydrobromic acid, or by reacting with potassium iodide. In a nonaqueous fashion, the hydrochloride is conventionally reacted with isoamyl nitrite and, for example, methylene iodide or bromoform in aprotic solvents, such as dimethylformamide. Introduction of fluorine is accomplished, for example, by the Balz-Schiemann reaction of the diazonium tetrafluoroborate.

Reaction of the amino group with 2-aza-butadienes of Formula IV to the imidazole derivatives takes place in the presence of acids at temperatures of 0–150° C. The leaving groups U and V can be identical or different; especially suitable are $C_{1-3}$ dialkylamines, such as dimethyl-, diethyl- and dipropylamine, and cyclic amines, such as pyrrolidine.

The reaction is performed, for example, in such a way that the amine derivative and the azadiene are first of all stirred in an organic acid, e.g. formic acid, acetic acid, propionic acid or trifluoroacetic acid, at room temperature and then are heated up to the boiling temperature of the reaction mixture (up to about 120° C.).

The acid can serve simultaneously as the reactant and also as the solvent. However, it is also possible to add solvents, such as, for example, alcohols, ethers, ketones, esters, such as ethyl acetate, hydrocarbons, such as toluene, or halogenated hydrocarbons, such as carbon tetrachloride.

The quantity of acid can be varied within wide limits, but the acid is utilized in excess. Preferably, a three- to tenfold excess of acid, based on the amine and the azadiene, is chosen.

The isomer mixtures can be separated into the enantiomers or E/Z isomers in accordance with conventional methods, such as, for example, crystallization, chromatography or conversion into diastereomers, such as, for example, salt formation.

The salts are prepared in the usual way by combining a solution of the compound of Formula I with the equivalent amount or an excess of an alkali or alkaline earth compound which is optionally in solution and by separating the precipitate, or working up the solution in the usual way.

Insofar as the production of the starting compounds is not described, they are known or can be prepared analogously to known methods or to processes described herein.

For example, the compounds of Formula II can be produced by preparing 2,4-dinitroarylamines according to the Sanger method by reacting o-halogen-nitroaromatics, preferably o-fluoronitroaromatics, e.g. dinitrofluorobenzene, in an aqueous solution with amino acid derivatives in the presence of a base, such as sodium carbonate or sodium bicarbonate at temperatures of between 0° C. up to reflux, and subsequently reducing these products. This reaction can be transferred also to other substituted 2-nitrohalogen compounds. Diarylamino compounds can also be obtained by Ullmann reaction of dinitrochlorobenzene with an aromatic amine. For this reaction, high-boiling solvents are utilized, such as dimethylformamide or collidine, and solid potassium carbonate and powdered copper as the base. It is also possible to produce the corresponding o-nitroanilines by alkylation or with substituted aldehydes by reductive alkylation. The subsequent reduction of the o-nitro group takes place in the presence of several nitro groups selectively by sodium sulfide in the presence of ammonia, as well as ammonium chloride, in polar solvents at room temperature or elevated temperature. In some cases, it is advantageous to effect the reaction with esters and to hydrolyze the latter in a final step.

The separation of enantiomers can take place at the final stage or in the intermediate stages by optically active auxiliary bases, such as, for example, brucine or 1-phenethylamine, or also by chromatography via optically active carrier materials. The enantiomers can, however, also be produced synthetically by reacting the corresponding optically active amino acids with the corresponding fluoronitroaromatics according to the Sanger method and further processing of the aminonitroaromatics as described above.

Without further elaboration, it is believed that one skilled in the art can, using the preceding description, utilize the present invention to its fullest extent. The preferred specific embodiments are, therefore, to be construed as merely illustrative, and not limitative of the disclosure in any way whatsoever.

The entire disclosure of all applications, patents and publications, cited above, and of corresponding German applications P 41 35 871.6 and P 42 24 200.2, are hereby incorporated by reference.

EXAMPLES

Example 1

3-(6-Nitro-2,3-dioxo-1,2,3,4-tetrahydroquinoxalin-1-ylmethyl) benzoic Acid Methyl Ester and 3-(7-Nitro-2,3-dioxo-1,2,3,4-tetrahydroquinoxalin-1-ylmethyl) benzoic Acid Methyl Ester Under an $N_2$ stream and exclusion of moisture, 1.03 g (5 millimoles) of 6-nitro-2,3-dioxo-1,2,3,4-tetrahydroquinoxaline is combined with 50 ml of dimethylformamide at room temperature. To this mixture is added 330 mg (11 mmol) of sodium hydride (80% strength) in 3 portions. The mixture is then stirred for one hour at room temperature. To this mixture is added dropwise 1.26 g (5.5 mmol) of 3-bromomethyl-benzoic acid methyl ester in 5 ml of dimethylformamide, and the mixture is further stirred for 3½ hours. After concentration, the residue is distributed in acetic water/ethyl acetate. The organic phase is separated, dried, filtered and concentrated. The residue is chromatographed over silica gel with dichloromethan:ethanol=95:5, thus obtaining, besides 211 mg of 3-(6-nitro-2,3-dioxo-1,2,3,4-tetrahydroquinoxalin-1-yl-methyl)benzoic acid methyl ester, which is not further purified, also 222 mg of 3-(7-nitro-2,3-dioxo-1,2,3,4-tetrahydroquinoxalin-1-ylmethyl) benzoic acid methyl ester, mp: 265–267° C.

The following compounds are produced analogously:
4-(6-nitro-2,3-dioxo-1,2,3,4-tetrahydroquinoxalin-1-ylmethyl)benzoic acid methyl ester, mp: 308–314° C.,
4-(7-nitro-2,3-dioxo-1,2,3,4-tetrahydroquinoxalin-1-ylmethyl)benzoic acid methyl ester, mp: >300° C.,
2-(6-nitro-2,3-dioxo-1,2,3,4-tetrahydroquinoxalin-1-ylmethyl)benzoic acid ethyl ester, mp: 279°/283–284° C.,
2-(7-nitro-2,3-dioxo-1,2,3,4-tetrahydroquinoxalin-1-ylmethyl)benzoic acid ethyl ester (further processed without further purification), 1-(3-methoxycarbonyl-2-propenyl)-6-nitroquinoxaline-2,3-(1H,4H)-dione, mp: 258–265° C. with decomposition,
1-(3-ethoxycarbonylpropyl)-6-nitroquinoxaline-2,3-(1H,4H)-dione, mp: 215–217° C.,
1-(3-ethoxycarbonylpropyl)-7-nitroquinoxaline-2,3-(1H,4H)-dione, mp: 215–217° C.,
4-(6-nitro-2,3-dioxo-1,2,3,4-tetrahydroquinoxalin-1-ylmethyl)phenylphosphonic acid diethyl ester, mp: 114° C. /129–131° C.,
4-(7-nitro-2,3-dioxo-1,2,3,4-tetrahydroquinoxalin-1-ylmethyl)phenylphosphonic acid diethyl ester (further processed without purification),
3-(6-trifluoromethyl-2,3-dioxo-1,2,3,4-tetrahydroquinoxaline -1-yl)prop-1-ene-1-phosphonic acid diethyl ester,
3-(6-trifluoromethyl-2,3-dioxo-1,2,3,4-tetrahydroquinolin-1-yl)prop-1-yne-1-phosphonic acid diethyl ester,
3-(6-nitro-2,3-dioxo-1,2,3,4-tetrahydroquinoxalin-1-yl)propane-1-phosphonic acid diethyl ester,
1-(6-trifluoromethyl-2,3-dioxo-1,2,3,4-tetrahydroquinoxalin -1-yl)methanecarboxylic acid tert-butyl ester.

Example 2

With twice the amount of methyl-3-bromomethyl benzoate and otherwise identical conductance of the reaction as in Example 1, it is furthermore possible to isolate 503 mg of 3-[4-(3-methoxycarbonylbenzyl)-6-nitro-2,3-dioxo-1,2,3,4-tetrahydroquinoxalin-1-yl -methyl] benzoic acid, mp: 238–240° C.

The following compounds are produced analogously:
4-[4-(4-methoxycarbonylbenzyl)-6-nitro-2,3-dioxo -1,2,3,4-tetrahydroquinoxalin-1-ylmethyl] benzoic acid methyl ester, mp: 225–227° C.

Example 3

(A) 4-(2,4-Dinitrophenyl)aminobenzoic Acid Ethyl Ester

At a bath temperature of 180° C. under argon and with exclusion of moisture, 1.01 g (5 mmol) of 1-chloro-2,4-dinitrobenzene, 1.01 g (6 mmol) of 4-aminobenzoic acid ethyl ester, 13 mg (0.2 mmol) of pulverized copper, and 961 mg (7 mmol) of potassium carbonate (pulverized) are stirred for 25 minutes in 5 ml of absolute dimethylformamide.

After concentration, the mixture is poured into water, rendered alkaline with ammonia, extracted by shaking with ethyl acetate, and the organic phase is separated, filtered and concentrated. The residue is chromatographed over silica gel with cyclohexane: ethyl acetate =8:2, thus obtaining 768 mg of 4-(2,4-dinitrophenyl)aminobenzoic acid ethyl ester, mp: 99–102° C.

The following compounds are prepared analogously:
3-(2,4-dinitrophenyl)aminobenzoic acid ethyl ester, mp: 108–110° C.,
3-(2,4-dinitrophenyl)aminophenylphosphonic acid ethyl ester, further processed without purification,
2-(2,4-dinitrophenyl)aminobenzoic acid ethyl ester, further processed without purification.

(B) 4-(2-Amino-4-nitrophenylamino)benzoic Acid Ethyl Ester

At an internal temperature of 78° C. (90° C. bath temperature), 566 mg (1.7 mmol) of 4-(2,4-dinitrophenylamino)benzoic acid ethyl ester, 761 mg (12.2 mmol) of ammonium chloride, 0.68 ml of concentrated ammonia, 15 ml of ethanol and 6 ml of distilled water are combined. To this mixture is added 1.27 g (5.68 mmol) of sodium sulfide (35% strength) in 3 portions, and the mixture is stirred for one hour. The batch is vacuum-filtered at room temperature and first washed with water and then under ether, thus obtaining 535 mg of 4-(2-amino-4-nitrophenylamino)benzoic acid ethyl ester as the crude product (processed without further purification).

The following compounds are prepared in analogous fashion:
3-(2-amino-4-nitrophenylamino)benzoic acid ethyl ester, mp: 145–150° C.,
3-(2-amino-4-nitrophenylamino)phenylphosphonic acid ethyl ester, mp: 160–163° C.

(C) 4-(6-Nitro-2,3-dioxo-1,2,3,4-tetrahydroquinoline -1-yl) benzoic Acid Ethyl Ester At a bath temperature of +40° C., under argon and with exclusion of moisture, 582 mg (2.3 mmol) of 4-(2-amino-4-nitrophenylamino)benzoic acid ethyl ester is combined with 488 mg (4.8 mmol) of triethylamine in 27 ml of dry tetrahydrofuran. A solution of 659 mg (4.8 mmol) of oxalic acid ethyl ester chloride and 8 ml of dry tetrahydrofuran is added dropwise to this batch and stirred for 2 hours at room temperature. The mixture is then combined with 0.2 ml of triethylamine and 0.1 ml of oxalic acid ethyl ester chloride, and agitated for one hour at room temperature. The batch is filtered, and the filtrate is concentrated and distributed in water/ethyl acetate. The organic phase is concentrated. The residue is refluxed for 2 hours at the bath temperature in 25 ml of 1N hydrochloric acid and 25 ml of ethanol. The thus-precipitated product is suctioned off, washed with water, and dried, yielding 220 mg of 4-(6-nitro-2,3-dioxo-1,2,3,4-tetrahydroquinoxalin-1-yl)benzoic acid ethyl ester (further processed without purification).

The following compounds are produced analogously:
3-(6-nitro-2,3-dioxo-1,2,3,4-tetrahydroquinoxalin-1-yl) benzoic acid ethyl ester, mp: 258–263° C.,
3-(6-nitro-2,3-dioxo-1,2,3,4-tetrahydroquinoxalin-1-yl) phenylphosphonic acid ethyl ester.

Example 4

(A) 2-(2,4-Dinitrophenyl)aminobenzoic Acid

At a bath temperature of 40° C., 1.37 g (10 mmol) of 2-aminobenzoic acid and 2 g (18.7 mmol) of sodium carbonate in 40 ml of water are combined under vigorous stirring with 1.86 g (10 mmol) of 2,4-dinitrofluorobenzene and agitated for 2 hours. The batch is diluted with about 400 ml of water and precipitated with 4N HCl. The product is suctioned off, washed with water, and dried, thus obtaining 2.8 g of 2-(2,4-dinitrophenyl)aminobenzoic acid, mp: 266–270° C.

The following compounds are prepared analogously:
3-(2,4-dinitrophenylamino)propionic acid, mp: 134–137° C.,
4-(2,4-dinitrophenylamino)phenylphosphonic acid, mp: 271–272° C. with decomposition,
2-(2,4-dinitrophenylamino)phenylphosphonic acid, further processed without purification,
(2,4-dinitrophenylamino)methanephosphonic acid, mp: 225–227° C.,
2-(2,4-dinitrophenylamino)ethanephosphonic acid, further processed without purification,
3-(2,4-dinitrophenylamino)phenylphosphonic acid,
(2-nitro-1-naphthylamino)methanephosphonic acid,
(1-nitro-2-naphthylamino)methanephosphonic acid,
1-(2-nitro-1-naphthylamino)ethane-1-phosphonic acid,
1-(1-nitro-2-naphthylamino)ethane-1-phosphonic acid,
(2-nitro-4-trifluoromethylphenylamino)methanephosphonic acid,
1-(2-nitro-4-trifluoromethylphenylamino)ethane-1-phosphonic acid,
1-(2,4-dinitrophenylamino)ethane-1-phosphonic acid, 3-(2,4-dinitrophenylamino)propane-1-phosphonic acid,
4-(2,4-dinitrophenylamino)butane-1-phosphonic acid,
(2-nitro-4-fluorophenylamino)methanephosphonic acid,
(2-nitro-4-chlorophenylamino)methanephosphonic acid,
(2-nitro-4-bromophenylamino)methanephosphonic acid,
(2-nitro-4-methylphenylamino)methanephosphonic acid,
1-(2-nitro-4-fluorophenylamino)ethane-1-phosphonic acid,
1-(2-nitro-4-chlorophenylamino)ethane-1-phosphonic acid,
1-(2-nitro-4-bromophenylamino)ethane-1-phosphonic acid,
1-(2-nitro-4-methylphenylamino)ethane-1-phosphonic acid,
1-phenyl-1-(2-nitro-4- trifluoromethylphenylamino)-methanephosphonic acid,
1-methyl-1-(2-nitro-4-trifluoromethylphenylamino)-ethane-1-phosphonic acid,
1-(2-nitro-4-trifluoromethylphenylamino) hexane-1-phosphonic acid,
1-methyl-2-(2-nitro-4-trifluoromethylphenylamino)-ethane-1-phosphonic acid,
2-(2-nitro-4-trifluoromethylphenylamino)propane-1-phosphonic acid,
1-methyl-2-(2-nitro-4-trifluoromethylphenylamino)-propane-1-phosphonic acid,
1-(2-nitro-4-trifluoromethylphenylamino) cylopropane-1-phosphonic acid,
(+)-1-(2-nitro-4-trifluoromethylphenylamino)ethane-1-phosphonic acid,
(−)-1-(2-nitro-4-trifluoromethylphenylamino)ethane-1-phosphonic acid,
P,P-dimethyl-(2,4-dinitrophenylamino)methanephosphinoxide,
P-methyl-(2,4-dinitrophenylamino)methanephosphinic acid,
1-[5-(imidazol-1-yl)-2,4-dinitrophenylamino] methylphosphonic acid,
1-[5-(imidazol-1-yl)-2-nitro-4-trifluoromethylphenylamino] methylphosphonic acid.

(B) 1-[5-(Imidazol-1-yl)-2,4-dinitrophenylamino]-ethane-1-phosphonic Acid

At 40° C., 600 mg of 5-fluoro-2,2-dinitrofluorobenzene is combined with 30 ml of water and 10 ml of ethanol and mixed dropwise with a solution of 376 mg of rac. amino-ethylphosphonic acid in 10 ml of water and 600 mg of sodium carbonate. The mixture is stirred for 1.5 hours at the temperature. After removal of the ethanol by distillation, the mixture is extracted against acetic acid. The aqueous phase is combined with 200 mg of imidazole and heated for 2 hours to 110° C. An additional 200 mg of imidazole is added and the mixture is heated for 2 hours to 110°. The mixture is acidified with 4N hydrochloric acid, suctioned off from undissolved matter, and the filtrate is washed with ethyl acetate. The aqueous phase is concentrated and extracted by boiling with ethanol. The ethanol extract is concentrated and chromatographed over silica gel with methanol:butanol:water:ammonia=75:25:17:3, yielding 300 mg of 1-[5-(imidazol-1-yl)-2,4-dinitrophenylamino]-ethane-1-phosphonic Acid.

(C) 2-(2-Amino-4-nitrophenylamino)benzoic Acid 1.80 g (6 mmol) of 2-(2,4-dinitrophenylamino)benzoic acid, 2.66 g (42.6 mmol) of ammonium chloride, 2.4 ml of ammonia, concentrated, 52 ml of ethanol, and 21 ml of distilled water are combined at an internal temperature of 78° C. (bath temperature 90° C.). To this batch is added, in 3 portions, 4.44 g (20 mmol) of sodium sulfide (35% strength) and the mixture is stirred for one hour. The batch is suctioned off at room temperature and washed in succession with water and ether. The filtrate is concentrated to the aqueous phase and extracted by shaking with ethyl acetate. The organic phase is dried, filtered, and concentrated. The aqueous phase is acidified with 1N hydrochloric acid and suctioned off, thus obtaining 1.1 g of 2-(2-amino-4-nitrophenylamino)benzoic acid (processed without purification).

The following compounds are produced analogously and further processed without purification:
3-(2-amino-4-nitrophenylamino)propionic acid,
4-(2-amino-4-nitrophenylamino)phenylphosphonic acid,
2-(2-amino-4-nitrophenylamino)phenylphosphonic acid,
(2-amino-4-nitrophenylamino)methylphosphonic acid,
(2-amino-4-nitrophenylamino)ethylphosphonic acid,
1-(2-amino-4-nitrophenylamino)ethane-1-phosphonic acid,
3-(2-amino-4-nitrophenylamino)propane-1-phosphonic acid,
4-(2-amino-4-nitriphenylamino)butane-1-phosphonic acid,
1-(2-amino-4-trifluoromethylphenylamino)cyclopropane-1-phosphonic acid,
P,P-dimethyl-(2-amino-4-nitrophenylamino) methanephosphinoxide,
P-methyl-(2-amino-4-nitrophenylamino) methanephosphinic acid,
1-[5-(imidazol-1-yl)-2-amino-4-nitrophenylamino] methylphosphonic acid.

(D) (2-Amino-4-trifluoromethylphenylamino) methanephosphonic Acid

In 180 ml of ethanol, 894 mg of (2-NO$_2$-4-trifluoromethylphenylamino)methanephosphonic acid is combined with 3 g of Raney nickel and hydrogenated for 3 hours at room temperature under hydrogen normal pressure. The batch is suctioned off from the catalyst and the filtrate concentrated. The compound is utilized in step (E) without further purification.

The following compounds are prepared in a basically analogous fashion:
1-(2-amino-1-naphthylamino)ethane-1-phosphonic acid,
1-(1-amino-2-naphthylamino)ethane-1-phosphonic acid,
1-(2-amino-1-naphthylamino)methanephosphonic acid,
1-(1-amino-2-naphthylamino)methanephosphonic acid,
1-(2-amino-4-trifluoromethylphenylamino)ethane-1-phosphonic acid,
1-(2-amino-4-trifluoromethylphenylamino)methane-1-phosphonic acid,
(2-amino-4-methylphenylamino)methanephosphonic acid,
1-(2-amino-4-methylphenylamino)ethane-1-phosphonic acid,
1-phenyl-1-(2-amino-4-trifluoromethylphenylamino)-methanephosphonic acid,
1-methyl-1-(2-amino-4-trifluoromethylphenylamino)-ethane-1-phosphonic acid,
1-(2-amino-4-trifluoromethylphenylamino)hexane-1-phosphonic acid,
1-methyl-2-(2-amino-4-trifluoromethylphenylamino)-ethane-1-phosphonic acid,
2-(2-amino-4-trifluoromethylphenylamino)propane-1-phosphonic acid,
1-methyl-2-(2-amino-4-trifluoromethylphenylamino)-propane-1-phosphonic acid,
(+)-1-(2-amino-4-trifluoromethylphenylamino)ethane-1-phosphonic acid,
(−)-1-(2-amino-4-trifluoromethylphenylamino)ethane-1-phosphonic acid,
(4-chloro-2-aminophenylamino)methanephosphonic acid,
1-(4-chloro-2-aminophenylamino)ethane-1-phosphonic acid,
(4-fluoro-2-aminophenylamino)methanephosphonic acid,
[5-(imidazol-1-yl)-4-trifluoromethyl-2-aminophenylamino) methylyphosphonic acid, 1-(4-fluoro-2-aminophenylamino)ethane-1-phosphonic acid.

(E) 3-(6-Nitro-2,3-dioxo-1,2,3,4-tetrahydroquinoxalin-1-yl) propionic Acid

At a bath temperature of +40° C., under argon and with exclusion of moisture, 211 mg (0.9 mmol) of 3-(2-amino-4-nitrophenylamino)propionic acid is combined with 200 mg (2 mmol) of triethylamine in 20 ml of dry tetrahydrofuran. A solution of 270 mg (2 mmol) of oxalic acid ethyl ester chloride and 5 ml of dry tetrahydrofuran is added dropwise to the batch, and the latter is stirred for 2 hours at room temperature. Furthermore, 0.05 ml of triethylamine and 0.05 ml of oxalic acid ethyl ester chloride are added to the mixture and the latter stirred for one hour at room temperature. The batch is filtered and the filtrate concentrated and distributed in water and ethyl acetate. The organic phase is concentrated. The residue is taken up in 15 ml of ethanol and 15 ml of 1N hydrochloric acid and refluxed for 2 hours at a bath temperature of 110° C. The batch is concentrated, taken up in a small amount of water, and suctioned off, yielding 120 mg of 3-(6-nitro-2,3-dioxo-1,2,3,4-tetrahydroquinoxalin-1-yl)propionic acid, mp: 148–156° C. with decomposition.

The following compounds are prepared analogously:
2-(6-nitro-2,3-dioxo-1,2,3,4-tetrahydroquinoxalin-1-yl) benzoic acid, mp: >255° C.,
4-(6-nitro-2,3-dioxo-1,2,3,4-tetrahydroquinoxalin-1-yl) phenylphosphonic acid, mp: >252° C.,
2-(6-nitro-2,3-dioxo-1,2,3,4-tetrahydroquinoxalin-1-yl) phenylphosphonic acid, mp: >310° C.,
(6-nitro-2,3-dioxo-1,2,3,4-tetrahydroquinoxalin-1-yl)-methanephosphonic acid, mp: 180–200° C. with decomposition,
2-(6-nitro-2,3-dioxo-1,2,3,4-tetrahydroquinoxalin-1-yl) ethanephosphonic acid, mp: 304–308° C. with decomposition,
(2,3-dioxo-1,2,3,4-tetrahydrobenzo(f)quinoxalin-4-yl)-methanephosphonic acid,
(2,3-dioxo-1,2,3,4-tetrahydrobenzo(f)quinoxalin-4-yl) ethane-1-phosphonic acid,
(2,3-dioxo-1,2,3,4-tetrahydrobenzo(f)quinoxalin-1-yl)-methanephosphonic acid,
(2,3-dioxo-1,2,3,4-tetrahydrobenzo(f)quinoxalin-1-yl)-ethane-1-phosphonic acid,
(6-trifluoromethyl-2,3-dioxo-1,2,3,4-tetrahydroquinoxalin-1-yl)methanephosphonic acid, mp: 202° C.,
1-(6-trifluoromethyl-2,3-dioxo-1,2,3,4-tetrahydroquinoxalin-1-yl)ethanephosphonic acid, mp: 274° C.,
1-(6-nitro-2,3-dioxo-1,2,3,4-tetrahydroquinoxalin-1-yl) ethane-1-phosphonic acid, mp: 297–300° C. with decomposition,
3-(6-nitro-2,3-dioxo-1,2,3,4-tetrahydroquinoxalin-1-yl) propane-1-phosphonic acid, mp: 200° C. with foaming,
4-(6-nitro-2,3-dioxo-1,2,3,4-tetrahydroquinoxalin-1-yl) butane-1-phosphonic acid, mp: 285–287° C.,
(6-fluoro-2,3-dioxo-1,2,3,4-tetrahydroquinoxalin-1-yl) methanephosphonic acid,
(6-chloro-2,3-dioxo-1,2,3,4-tetrahydroquinoxalin-1-yl) methanephosphonic acid,
(6-bromo-2,3-dioxo-1,2,3,4-tetrahydroquinoxalin-1-yl) methanephosphonic acid,
(6-methyl-2,3-dioxo-1,2,3,4-tetrahydroquinoxalin-1-yl) methanephosphonic acid,
1-(6-fluoro-2,3-dioxo-1,2,3,4-tetrahydroquinoxalin-1-yl) ethane-1-phosphonic acid, mp: 259° C.,
1-(6-chloro-2,3-dioxo-1,2,3,4-tetrahydroquinoxalin-1-yl) ethane-1-phosphonic acid,
1-(6-bromo-2,3-dioxo-1,2,3,4-tetrahydroquinoxalin-1-yl) ethane-1-phosphonic acid,
1-(6-methyl-2,3-dioxo-1,2,3,4-tetrahydroquinoxalin-1-yl) ethane-1-phosphonic acid,
1-(6-trifluoromethyl-2,3-dioxo-1,2,3,4-tetrahydroquinoxalin-1-yl)-1-phenylmethane-1-phosphonic acid, mp: 245° C.,
1-(6-trifluoromethyl-2,3-dioxo-1,2,3,4-tetrahydroquinoxalin-1-yl)-1-methylethanephosphonic acid,
1-(6-trifluoromethyl-2,3-dioxo-1,2,3,4-tetrahydoquinoxalin-1-yl)hexane-1-phosphonic acid,
1-methyl-2-(6-trifluoromethyl-2,3-dioxo-1,2,3,4-tetrahydroquinoxalin-1-yl)ethane-1-phosphonic acid,
2-(6-trifluoromethyl-2,3-dioxo-1,2,3,4-tetrahydroquinoxalin-1-yl)propane-1-phosphonic acid,
1-methyl-2-(6-trifluoromethyl-2,3-dioxo-1,2,3,4-tetrahydroquinoxalin-1-yl)propane-1-phosphonic acid,
1-(6-trifluoromethyl-2,3-dioxo-1,2,3,4-tetrahydroquinoxalin-1-yl) cyclopropane-1-phosphonic acid,
(+)-1-(6-trifluoromethyl-2,3-dioxo-1,2,3,4-tetrahydroquinoxalin-1-yl)ethane-1-phosphonic acid, $[\alpha_{546}^{20}]=+7.4°$ (c=0.505; $H_2O$),
(−)-1-(6-trifluoromethyl-2,3-dioxo-1,2,3,4-tetrahydroquinoxalin-1-yl)ethane-1-phosphonic acid, $[\alpha_{546}^{20}]=-5.9°$ (c=0.510; $H_2O$),
P-[methyl-(6-nitro-2,3-dioxo-1,2,3,4-tetrahydroquinoxalin-1-yl)methanephosphinic acid, mp: 320–325° C. with decomposition,
P,P-dimethyl-(6-nitro-2,3-dioxo-1,2,3,4-tetrahydroquinoxalin-1-yl)methanephosphinoxide, mp: 325–330° C. with decomposition,
(6-nitro-7-(imidazol-1-yl)-2,3-dioxo-1,2,3,4-tetrahydroquinoxalin-1-yl)methylphosphonic acid,
(6-trifluoromethyl-7-(imidazol-1-yl)-2,3-dioxo-1,2,3,4-tetrahydroquinoxalin-1-yl)methylphosphonic acid.

Example 5

3-(6-Nitro-2,3-dioxo-1,2,3,4-tetrahydroquinoxalin-1-yl-methyl) benzoic Acid 211 mg (0.6 mmol) of 3-(6-nitro-2,3-dioxo-1,2,3,4-tetrahydroquinoxalin-1-ylmethyl)benzoic acid methyl ester is combined with 4 ml of 4N hydrochloric acid, mixed with 4 ml of trifluoroacetic acid, and stirred for 3½ hours at a bath temperature of 110° C. The batch is diluted with water, after cooling to room temperature, and suctioned off. The filter cake is washed with water and ethanol and dried. Yield: 179 mg of 3-(6-nitro-2,3-dioxo-1,2,3,4-tetrahydroquinoxalin-1-ylmethyl)benzoic acid, mp: >330° C.

The following compounds are prepared in analogy:
3-(7-nitro-2,3-dioxo-1,2,3,4-tetrahydroquinoxalin-1-ylmethyl)benzoic acid, mp: >330° C.,
3-[4-(3-carboxybenzyl)-6-nitro-2,3-dioxo-1,2,3,4-tetrahydroquinoxalin-1-ylmethyl]benzoic acid, mp: 298–300° C.,
2-(6-nitro-2,3-dioxo-1,2,3,4-tetrahydroquinoxalin-1-ylmethyl)benzoic acid, mp: 329–334° C. with decomposition,
2-(7-nitro-2,3-dioxo-1,2,3,4-tetrahydroquinoxalin-1-ylmethyl)benzoic acid, mp: 328–330° C.,
2-[4-(2-carboxybenzyl)-6-nitro-2,3-dioxo-1,2,3,4-tetrahydroquinoxalin-1-ylmethyl)benzoic acid, mp: >300° C.,
4-(6-nitro-2,3-dioxo-1,2,3,4-tetrahydroquinoxalin-1-ylmethyl)benzoic acid, mp: >310° C., 4-(7-nitro-2,3-dioxo-1,2,3,4-tetrahydroquinoxalin-1-ylmethyl)benzoic acid, mp: 320–324° C. with decomposition, 4-[4-(4-carboxymethylbenzyl)-6-nitro-2,3-dioxo-1,2,3,4-tetrahydroquinoxalin-1-ylmethyl]benzoic acid, mp: >310° C., 4-(6-nitro-2,3-dioxo-1,2,3,4-tetrahydroquinoxalin-1-yl)benzoic acid, mp: >345° C., 3-(6-nitro-2,3-dioxo-1,2,3,4-tetrahydroquinoxalin-1-yl)benzoic acid, mp: >250° C., 1-(3-carboxy-2-propenyl)-6-nitroquinoxaline-2,3-(1H, 4H)-dione, mp: 242–243° C., 1,4-bis(3-carboxy-2-propenyl)-6-nitroquinoxaline-2,3-(1H, 4H)-dione, mp: 241–247° C. with decomposition, 1-(3-carboxypropyl)-6-nitroquinoxaline-2,3-(1H, 4H)-dione, mp: 230–232° C., 1-(3-carboxypropyl)-7-nitroquinoxaline-2,3-(1H, 4H)-dione, mp: 325–327° C. with decomposition, 1-(6-trifluoromethyl-2,3-dioxo-1,2,3,4-tetrahydroquinoxalin-1-yl)acetic acid, mp: 320° C.

Example 6

4-(6-Nitro-2,3-dioxo-1,2,3,4-tetrahydroquinoxalin-1-ylmethyl)phenylphosphonic Acid 582 mg (1.4 mmol) of 4-(6-nitro-2,3-dioxo-1,2,3,4-tetrahydroquinoxalin-1-ylmethyl)phenylphosphonic acid ethyl ester is refluxed in 6 ml of concentrated hydrochloric acid for 2 hours. After cooling, the batch is combined with water and suctioned off. The filter cake is dried, thus obtaining 253 mg of 4-(6-nitro-2,3-dioxo-1,2,3,4-tetrahydroquinoxalin-1-ylmethyl)phenylphosphonic acid, mp: 253–265° C. with decomposition.

The following compounds are produced analogously:
4-(7-nitro-2,3-dioxo-1,2,3,4-tetrahydroquinoxalin-1-ylmethyl)phenylphosphonic acid, mp: >250° C., 3-(6-nitro-2,3-dioxo-1,2,3,4-tetrahydroquinoxalin-1-yl)phenylphosphonic acid, mp: 304–307° C. with decomposition, 3-(6-trifluoromethyl-2,3-dioxo-1,2,3,4-tetrahydroquinoxalin-1-yl)prop-1-yne-1-phosphonic acid, 3-(6-trifluoromethyl-2,3-dioxo-1,2,3,4-tetrahydroquinoxalin-1-yl)prop-1-ene-1-phosphonic acid.

Example 7

(6-Nitro-2,3-dioxo-1,2,3,4-tetrahydroquinoxalin-1-yl)-methanephosphonic Acid Monoethyl As Well as Diethyl Ester At −15° C., 0.29 ml (476 mg) of thionyl chloride is added dropwise to 300 mg of (6-nitro-2,3-dioxo-1,2,3,4-tetrahydroquinoxalin-1-yl)methanephosphonic acid in 5 ml of absolute dimethylformamide. After this addition step is finished, the batch is stirred at a bath temperature of +4° C. for 20 minutes. Subsequently, 0.35 ml (276 mg) of ethanol is added to the batch and the latter is stirred for 1.5 hours at room temperature.

After concentration under vacuum, the product is chromatographed over silica gel with toluene: glacial acetic acid:water =10:10:1, thus obtaining first of all 100 mg of (6-nitro-2,3-dioxo-1,2,3,4-tetrahydroquinoxalin-1-yl)methanephosphonic acid diethyl ester, mp: 220–260° C. and then 36 mg of (6-nitro-2,3-dioxo-1,2,3,4-tetrahydroquinoxalin-1-yl)-methanephosphonic acid monoethyl ester, mp: 197° C.

The following compounds are prepared analogously:
(6-nitro-2,3-dioxo-1,2,3,4-tetrahydroquinoxalin-1-yl)-methanephosphonic acid mono-N,N-dimethylamide, and also bis-N,N-dimethylamide.

Example 8

1-(6-Amino-2,3-dioxo-1,2,3,4-tetrahydroquinoxalin-1-yl)methanephosphonic Acid 300 mg of 1-(6-nitro-2,3-dioxo-1,2,3,4-tetrahydroquinoxalin-1-yl)methanephosphonic acid is dissolved in 60 mg of methanol and combined under nitrogen in succession with 50 mg of Pd/C (10%), 300 mg of ammonium formate, and 18 ml of water, and heated for one hour to 80° C. After cooling, the mixture is filtered off from the catalyst, the filtrate is concentrated by evaporation, and the residue is freeze-dried, thus obtaining 200 mg of 1-(6-amino-2,3-dioxo-1,2,3,4-tetrahydroquinoxalin-1-yl)methanephosphonic acid in the form of a white solid.

The following compound is produced analogously:
1-(6-amino-2,3-dioxo-1,2,3,4-tetrahydroquinoxalin-1-yl)ethanephosphonic acid.

Example 9

1-[6-(4-Carbethoxyimidazol-1-yl)-2,3-dioxo-1,2,3,4-tetrahydroquinoxalin-1-yl]methanephosphonic Acid Under gentle cooling, 200 mg of 1,4-bis-dimethylamino-3-carbethoxy-2-azabutadiene-1,4 is combined with 3 ml of glacial acetic acid and stirred for 10 minutes at room temperature. Subsequently, 180 mg of 1-(6-amino-2,3-dioxo-1,2,3,4-tetrahydroquinoxalin-1-yl)methanephosphonic acid, dissolved in 3 ml of glacial acetic acid, is added to the batch and the latter stirred overnight at room temperature. The mixture is then heated for 4 hours to a bath temperature of 100° C. After concentration, 50 mg of 1-[6-(4-carbethoxyimidazol-1-yl)-2,3-dioxo-1,2,3,4-tetrahydroquinoxalin-1-yl]methanephosphonic acid is obtained as an oil.

The following compound is produced analogously:
1-[6-(4-cyano-5-methylimidazol-1-yl)-2,3-dioxo-1,2,3,4-tetrahydroquinoxalin-1-yl)methanephosphonic acid.

Example 10

1-(6-Iodo-2,3-dioxo-1,2,3,4-tetrahydroquinoxalin-1-yl)methanephosphonic Acid 180 mg of 1-(6-amino-2,3-dioxo-1,2,3,4-tetrahydroquinoxalin-1-yl)methanephosphonic acid is added dropwise to 10 ml of 25% strength sulfuric acid. After 5 minutes of agitation, a suspension of the salt is formed which is cooled to 0° C. To this is added a solution of 60 mg of sodium nitrite in 2 ml of water. After 15 minutes of stirring at 0° C., the reaction mixture is almost dissolved. To this is added a solution of 180 mg of potassium iodide in 2 ml of water. The ice bath is removed and the mixture heated to 100° C. for 2 hours. The cooled-off reaction mixture is neutralized with concentrated ammonia solution and evaporated to dryness. The residue is extracted by boiling with ethanol and a small amount of water, filtered, and the filtrate is concentrated. After chromatography over silanized silica gel with water:methanol=4:1, 40 mg of 1-(6-Iodo-2,3-dioxo-1,2,3,4-tetrahydroquinoxalin-1-yl)methanephosphonic acid is obtained, mp: 295–297° C.

The following compounds are obtained in analogous fashion or by analogous methods known from the literature:

1-(6-iodo-2,3-dioxo-1,2,3,4-tetrahydroquinoxalin-1-yl) ethane-1-phosphonic acid,
1-(6-bromo-2,3-dioxo-1,2,3,4-tetrahydroquinoxalin-1-yl) methanephosphonic acid,
1-(6-bromo-2,3-dioxo-1,2,3,4-tetrahydroquinoxalin-1-yl) ethane-1-phosphonic acid,
1-(6-cyano-2,3-dioxo-1,2,3,4-tetrahydroquinoxalin-1-yl) methanephosphonic acid.

Example 11

6-Iodo-2,3-dioxo-1,2,3,4-tetrahydroquinoxalin-1-yl-methanephosphonic Acid 100 mg of amino-2,3-dioxo-1,2,3,4-tetrahydroquinoxalin-1-ylmethanephosphonic acid is dissolved in concentrated hydrochloric acid and evaporated to dryness.

The hydrochloride is added in thoroughly dried form to 10 ml of dimethylformamide and combined-in succession with 4 ml of methylene iodide and 0.6 ml of isoamyl nitrite. After 2 hours at a bath temperature of 80° C., dissolution is complete. The mixture is concentrated in a bomb tube under vacuum, and the residue is chromatographed over silanized silica gel 60 (reversed phase) with water:methanol=4:1 as the mobile phase. Yield: 20 mg of 6-iodo-2,3-dioxo-1,2,3,4-tetrahydroquinoxalin-1-ylmethanephosphonic acid, mp: 295–297° C.

The following compounds are produced analogously:

6-bromo-2,3-dioxo-1,2,3,4-tetrahydroquinoxalin-1-yl-methanephosphonic acid,
1-(6-iodo-2,3-dioxo-1,2,3,4-tetrahydroquinoxalin-1-yl)-ethanephosphonic acid,
1- (6-bromo-2 3-dioxo-1,2,3,4-tetrahydroquinoxalin-1-yl)-ethanephosphonic acid.

Example 12

100 mg of 1-(6-amino-2,3-dioxo-1,2,3,4-tetrahydroquinoxalin-1-yl) methanephosphonic acid is adjusted in 20 ml of water to a pH of 9.5 with a saturated sodium carbonate solution and combined with 0.2 ml of acetic anhydride. After one hour of stirring, the mixture is concentrated, dissolved in a minimum amount of water, introduced into an ion exchanger (IR 120, strongly acidic), and eluted with water: The corresponding fractions are combined, concentrated, and dried, thus obtaining 110 mg of 1-(6-acetylamino-2,3-dioxo-1,2,3,4-tetrahydroquinoxalin-1-yl)methanephosphonic acid, mp: 120° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:
1. A compound of formula I

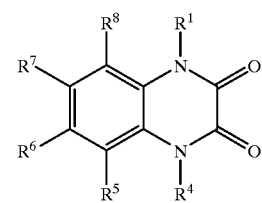

wherein
$R^1$ is $R^2$-substituted methyl, ethyl, propyl, isopropyl, butyl, isobutyl, sec-butyl, tert-butyl, pentyl, isopentyl, hexyl, heptyl, octyl, nonyl or decyl, $R^2$-substituted 2-propenyl, 2-butenyl, 3-methyl-2-propenyl, 1-propenyl, 1-butenyl or vinyl, $R^2$-substituted ethynyl, 1-propynyl, 2-propynyl or 1-butynyl, $R^2$-substituted cyclopropyl, cyclobutyl, cyclopentyl, cyclohexyl or cycloheptyl, —$(CH_2)_n$-phenyl-$(CH_2)_n$-naphthyl, —$(CH_2)_n$-biphenylyl or —$(CH_2)_n$-indenyl substituted by $R^2$ in the aryl or in the alkyl residue, or —$(CH_2)_n$-pyrazolyl, —$(CH_2)$ imidazolyl, —$(CH_2)_n$-pyrazinyl, —$(CH_2)_n$-pyridinyl, —$(CH_2)_n$-pyrimidinyl, —$(CH_2)_n$-pyridazinyl or —$(CH_2)_n$-triazinyl substituted by $R^2$ in the hetaryl or alkyl residue,
$R^4$ is hydrogen or $R^2$-substituted methyl, ethyl, propyl, isopropyl, butyl, isobutyl, sec-butyl, tert-butyl, pentyl, isopentyl, hexyl, heptyl, octyl, nonyl or decyl, $R^2$-substituted 2-propenyl, 2-butenyl, 3-methyl-2-propenyl, 1-propenyl, 1-butenyl or vinyl, $R^2$-substituted ethynyl, 1-propynyl, 2-propynyl or 1-butynyl, $R^2$-substituted cyclopropyl, cyclobutyl, cyclopentyl, cyclohexyl or cycloheptyl, —$(CH_2)_n$-phenyl-$(CH_2)$ naphthyl, —$(CH_2)_n$-biphenylyl or —$(CH_2)_n$-indenyl substituted by $R^2$ in the aryl or in the alkyl residue, or —$(CH_2)_n$-pyrazolyl, —$(CH_2)_n$-imidazolyl, —$(CH_2)_n$-pyrazinyl, —$(CH_2)_n$-pyridinyl, —$(CH_2)_n$-pyrimidinyl, —$(CH_2)_n$-pyridazinyl or —$(CH_2)$- triazinyl substituted by $R^2$ in the hetaryl or alkyl residue,
$R^5$, $R^6$, $R^7$ and $R^8$ are each independently hydrogen, halogen, nitro, $NHCOR^{11}$, $SO_2R^{12}$, $C_{3-7}$-cycloalkyloxy, $COR^{13}$, cyano, $CF_3$, $C_{1-6}$-alkyl, $C_{1-4}$-alkoxy, or imidazolyl optionally substituted by cyano, $C_{1-4}$-alkyl or —COO—$C_{1-6}$-alkyl,
$R^2$ is —CO—$R^3$ and is present once or twice,
n is 0, 1, 2, 3, 4 or 5,
$R^3$ is hydroxy, $C_{1-6}$-alkoxy or $NR^9R^{10}$,
$R^9$ and $R^{10}$ are each independently hydrogen, $C_{1-4}$-alkyl, or jointly with the nitrogen form a saturated 5- or 6-membered heterocycle which is piperidine, pyrrolidine, morpholine, thiomorpholine or piperazine,
$R^{11}$ is $C_{1-6}$-alkyl or phenyl,
$R^{12}$ is hydrogen, $C_{1-4}$-alkyl, $NH_2$, $N(C_{1-4}$-alkyl$)_2$,
$R^{13}$ is hydroxy, $C_{1-6}$-alkoxy, $C_{1-6}$-alkyl or $NR^9R^{10}$,
or a tautomer, optical isomer, or a racemic or enantiomeric mixture thereof, or a physiologically acceptable salt thereof,
and wherein,
if $R^1$ is methyl, ethyl, propyl, isopropyl, butyl, isobutyl, sec-butyl, tert-butyl, pentyl, isopentyl, hexyl, heptyl, octyl, nonyl or decyl substituted by —$COR^3$, then at least one of $R^5$, $R^6$, $R^7$ or $R^8$ is not hydrogen and at least three of $R^5$, $R^6$, $R^7$ or $R^8$ are not halogen;

if $R^1$ is —$CH_2$—COOH,
then $R^6$ and $R^7$ are not simultaneously $CH_3$,
$R^6$ is not $NO_2$ wherein $R^5$, $R^7$ and $R^8$ are each hydrogen, and
$R^7$ is not $NO_2$ where $R^5$, $R^6$ and $R^8$ are each hydrogen;

if $R^1$ is —$CH_2$—$COOC_2H_5$,
then $R^6$ is not $NO_2$ where $R^5$, $R^7$ and $R^8$ are each hydrogen,
$R^7$ is not $NO_2$ where $R^5$, $R^6$ and $R^8$ are each hydrogen; and if $R^1$ is —$COR^3$ substituted methyl, ethyl, propyl, isopropyl, butyl, isobutyl, sec-butyl, tert-butyl, pentyl, isopentyl, hexyl, heptyl, octyl, nonyl or decyl or —($CH_2$)-phenyl, —($CH_2$)-naphthyl, —($CH_2$)-biphenylyl or —($CH_2$)-indenyl substituted by —$COR^3$ in the aryl or in the alkyl residue and $R^4$ is H, then at least one of $R^5$, $R^6$, $R^7$ or $R^8$ is $NHCOR^{11}$, $SO_2R^{12}$, $C_{3-7}$-cycloalkyloxy or $COR^{13}$, and if $R^1$ is —$COR^3$-substituted methyl, ethyl, propyl, isopropyl, butyl, isobutyl, sec-butyl, tert-butyl, pentyl, isopentyl, hexyl, heptyl, octyl, nonyl or decyl, then $R^5$, $R^6$, $R^7$ and $R^8$ are not imidazolyl nor $NO_2$.

2. A compound of formula I

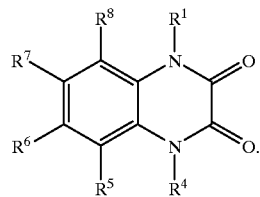

(I)

wherein
$R^1$ is $R^2$-substituted methyl, ethyl, propyl, isopropyl, butyl, isobutyl, sec-butyl, tert-butyl, pentyl, isopentyl, hexyl, heptyl, octyl, nonyl or decyl, $R^4$ is $R^2$-substituted methyl, ethyl, propyl, isopropyl, butyl, isobutyl, sec-butyl, tert-butyl, pentyl, isopentyl, hexyl, heptyl, octyl, nonyl or decyl, $R^2$-substituted 2-propenyl, 2-butenyl, 3-methyl-2-propenyl, 1-propenyl, 1-butenyl or vinyl, $R^2$-substituted ethynyl 1-propynyl, 2-propynyl or 1-butynyl, $R^2$-substituted cyclopropyl, cyclobutyl, cyclopentyl, cyclohexyl or cycloheptyl, —($CH_2$)$_n$-phenyl, —($CH_2$)$_n$-naphthyl, —($CH_2$)$_n$-biphenylyl or —($CH_2$)$_n$-indenyl substituted by $R^2$ in the aryl or in the alkyl residue, or —($CH_2$)$_n$-pyrazolyl, —($CH_2$)$_n$-imidazolyl, —($CH_2$)$_n$-pyrazinyl, —($CH_2$)$_n$-pyridinyl, —($CH_2$)$_n$-pyrimidinyl, —($CH_2$)$_n$-pyridazinyl or —($CH_2$)-triazinyl substituted in the hetaryl or alkyl residue, $R^5$, $R^6$, $R^7$ and $R^8$ are each independently hydrogen, $NHCOR^{11}$, $SO_2R^{12}$, $C_{3-7}$-cycloalkyloxy, $COR^{13}$, cyano, $CF_3$, $C_{1-6}$-alkyl or $C_{1-4}$-alkoxy, $R^2$ is —CO—$R^3$ and is present once or twice,
n is 0, 1, 2, 3, 4 or 5,
$R^3$ is hydroxy, $C_{1-6}$-alkoxy or $NR^9R^{10}$,
$R^9$ and $R^{10}$ are each independently hydrogen, $C_{1-4}$-alkyl, or jointly with the nitrogen form a saturated 5- or 6-membered heterocycle which is piperidine, pyrrolidine, morpholine, thiomorpholine or piperazine,
$R^{11}$ is $C_{1-6}$-alkyl or phenyl,
$R^{12}$ is hydrogen, $C_{1-4}$-alkyl, $NH_2$, $N(C_{1-4}$-alkyl)$_2$,
$R^{13}$ is hydroxy, $C_{1-6}$-alkoxy, $C_{1-6}$-alkyl or $NR^9R^{10}$,
or a tautomer, optical isomer, or a racemic or enantiomeric mixture thereof, or a physiologically acceptable salt thereof, wherein
at least one of $R^5$, $R^6$, $R^7$ or $R^8$ is not hydrogen;
if $R^1$ is —$CH_2$—COOH, then $R^6$ and $R^7$ are not simultaneously $CH_3$.

3. A compound of formula I

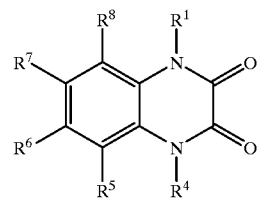

(I)

wherein
$R^4$ is hydrogen,
$R^1$ is $R^2$-substituted methyl, ethyl, propyl, isopropyl, butyl, isobutyl, sec-butyl, tert-butyl, pentyl, isopentyl, hexyl, heptyl, octyl, nonyl or decyl, —($CH_2$)$_n$-phenyl —($CH_2$)$_n$-naphthyl, —($CH_2$)$_n$-biphenylyl or —($CH_2$)$_n$-indenyl substituted by $R^2$ in the aryl or in the alkyl residue, $R^5$, $R^6$, $R^7$ and $R^8$ are each selected from the group consisting of $NHCOR^{11}$, $SO_2R^{12}$, $C_{3-7}$-cycloalkyloxy, $COR^{13}$, cyano or $CF_3$, hydrogen, halogen, nitro, $C_{1-6}$-alkyl, $C_{1-4}$-alkoxy, or imidazolyl optionally substituted by cyano, $C_{1-4}$-alkyl and —COO—$C_{1-6}$-alkyl;

wherein at least one of $R^5$, $R^6$, $R^7$ or $R^8$ is $NHCOR^{11}$, $SO_2R^{12}$, $C_{3-7}$-cycloalkyloxy, or $COR^{13}$, $R^2$ is —CO—$R^3$ and is present once or twice,
n is 0, 1, 2, 3, 4 or 5,
$R^3$ is hydroxy, $C_{1-6}$-alkoxy or $NR^9R^{10}$,
$R^9$ and $R^{10}$ are each independently hydrogen, $C_{1-4}$-alkyl, or jointly with the nitrogen form a saturated 5- or 6-membered heterocycle which is piperidine, pyrrolidine, morpholine, thiomorpholine or piperazine,
$R^{11}$ is $C_{1-6}$-alkyl or phenyl,
$R^{12}$ is hydrogen, $C_{1-4}$-alkyl, $NH_2$, $N(C_{1-4}$-alkyl)$_2$, and
$R^{13}$ is hydroxy, $C_{1-6}$-alkoxy, $C_{1-6}$-alkyl or $NR^9R^{10}$,
or a tautomer, optical isomer, or a racemic or enantiomeric mixture thereof, or a physiologically acceptable salt thereof.

4. A compound of formula I

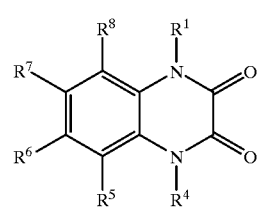

(I)

wherein
$R^4$ is hydrogen,
$R^1$ $R^2$-substituted 2-propenyl, 2-butenyl, 3-methyl-2-propenyl, 1-propenyl, 1-butenyl or vinyl, $R^2$-substituted ethynyl, 1-propynyl, 2-propynyl or 1-butynyl, $R^2$-substituted cyclopropyl, cyclobutyl, cyclopentyl, cyclohexyl or cycloheptyl, or —(CH$_2$)$_n$-pyrazolyl, —(CH$_2$)$_n$-imidazolyl, —(CH$_2$)$_n$-pyrazinyl, —(CH$_2$)$_n$-pyridinyl, —(CH$_2$)$_n$-pyrimidinyl, —(CH$_2$)$_n$-pyridazinyl or —(CH$_2$)-triazinyl substituted by R$^2$ in the hetaryl or alkyl residue, R$^5$, R$^6$, R$^7$ and R$^8$ are each independently NHCOR$^{11}$, SO$_2$R$^{12}$, C$_{3-7}$-cycloalkyloxy, COR$^{13}$, cyano or CF$_3$, hydrogen, halogen, nitro, C$_{1-6}$-alkyl, C$_{1-4}$-alkoxy, or imidazolyl optionally substituted by cyano, C$_{1-4}$-alkyl or —COO—C$_{1-6}$-alkyl;

R$^2$ is —CO—R$^3$ and is present once or twice, n is 0, 1, 2, 3, 4 or 5

R$^3$ is hydroxy, C$_{1-6}$-alkoxy, or NR$^9$R$^{10}$,

R$^9$ and R$^{10}$ are each independently hydrogen, C$_{1-4}$-alkyl, or jointly with the nitrogen form a saturated 5- or 6-membered heterocycle which is piperidine, pyrrolidine, morpholine, thiomorpholine or piperazine, R$^{11}$ is C$_{1-6}$-alkyl or phenyl, R$^{12}$ is hydrogen, C$_{1-4}$-alkyl, NH$_2$, N(C$_{1-4}$-alkyl)$_2$, and R$^{13}$ is hydroxy, C$_{1-6}$-alkoxy, C$_{1-6}$-alkyl or NR$^9$R$^{10}$, or a tautomer, optical isomer, or a racemic or enantiomeric mixture thereof, or a physiologically acceptable salt thereof.

5. A compound selected from the group consisting of 3-(6-Nitro-2,3-dioxo-1,2,3,4-tetrahydroquinoxalin-1-ylmethyl)benzoic acid methyl ester, 2-{4-(2-ethoxycarbonylbenzyl)-6-nitro-2,3-dioxo-1,2,3,4-tetrahydroquinoxalin-1-ylmethyl}benzoic acid ethyl ester, and 4-(6-nitro-2,3-dioxo-1,2,3,4-tetrahydroquinoxalin-1-yl)benzoic acid ethyl ester.

6. A pharmaceutical composition comprising a compound of claim 1 and a physiologically acceptable carrier.

7. A pharmaceutical composition comprising a compound of claim 2 and a physiologically acceptable carrier.

8. A pharmaceutical composition comprising a compound of claim 3 and a physiologically acceptable carrier.

9. A pharmaceutical composition comprising a compound of claim 4 and a physiologically acceptable carrier.

* * * * *

UNITED STATES PATENT AND TRADEMARK OFFICE
CERTIFICATE OF CORRECTION

PATENT NO. : 6,288,065 B1
DATED : September 11, 2001
INVENTOR(S) : Huth et al

It is certified that error appears in the above-identified patent and that said Letters Patent is hereby corrected as shown below:

Column 18,
Lines 25 and 38, reads "$(CH_2)$" should read -- $(CH_2)_n$ --

Signed and Sealed this

Fourth Day of March, 2003

JAMES E. ROGAN
*Director of the United States Patent and Trademark Office*